(12) United States Patent
Slaby et al.

(10) Patent No.: US 10,966,997 B2
(45) Date of Patent: Apr. 6, 2021

(54) METHODS FOR TREATING DEGENERATIVE DISC DISEASE AND CHRONIC LOWER BACK PAIN

(71) Applicant: DISCITISDX, INC., Aventura, FL (US)

(72) Inventors: Ondrej Slaby, Brno (CZ); Manu Capoor, New York, NY (US)

(73) Assignee: ECM DIAGNOSTICS, INC., Aventura, FL (US)

( * ) Notice: Subject to any disclaimer, the term of this patent is extended or adjusted under 35 U.S.C. 154(b) by 0 days.

(21) Appl. No.: 16/354,318

(22) Filed: Mar. 15, 2019

(65) Prior Publication Data
US 2019/0209597 A1    Jul. 11, 2019

Related U.S. Application Data

(63) Continuation-in-part of application No. PCT/US2018/052539, filed on Sep. 25, 2018.

(60) Provisional application No. 62/562,642, filed on Sep. 25, 2017, provisional application No. 62/572,027, filed on Oct. 13, 2017.

(51) Int. Cl.
| C07K 16/22 | (2006.01) |
| A61K 31/7056 | (2006.01) |
| A61P 31/04 | (2006.01) |
| A61K 39/395 | (2006.01) |
| C07K 16/24 | (2006.01) |

(52) U.S. Cl.
CPC ...... *A61K 31/7056* (2013.01); *A61K 39/3955* (2013.01); *A61P 31/04* (2018.01); *C07K 16/245* (2013.01)

(58) Field of Classification Search
CPC .... A61K 39/3955; A61P 31/04; C07K 16/245
See application file for complete search history.

(56) References Cited

FOREIGN PATENT DOCUMENTS

WO    2017019440 A1    2/2017

OTHER PUBLICATIONS

Knezevic et al., Treatment of Chronic Low Back Pain—New Approaches on the Horizon, Journal of Pain Research, 2017, vol. 10, pp. 1111-1123.
Slaby et al., "Is IL-1β Further Evidence for the Role of Propionibacterium acnes in Degenerative Disc Disease? Lessons From the Study of the Inflammatory Skin Condition Acne Vulgaris," Frontiers in Cellular and Infection Microbiology, 2018, vol. 8 No. 272, pp. 1-7.
International Search Report and Written Opinion for International Application No. PCT/US2018/052539, dated Nov. 26, 2018, 8 pages.

*Primary Examiner* — Robert C Hayes
(74) *Attorney, Agent, or Firm* — Morgan, Lewis & Bockius LLP

(57) ABSTRACT

The present invention in various aspects and embodiments provides methods for the treatment or prevention of degenerative disc disease or chronic lower back pain.

13 Claims, 8 Drawing Sheets

METHODS FOR TREATING DEGENERATIVE DISC DISEASE AND CHRONIC LOWER BACK PAIN

CROSS-REFERENCE TO RELATED APPLICATIONS

This application is a continuation-in-part of International Application No. PCT/US18/52539, which claims the benefit of U.S. Provisional Patent Application Nos. 62/562,642, filed Sep. 25, 2017, and 62/572,027, filed Oct. 13, 2017, the entire contents of which are herein incorporated by reference.

FIELD

The present invention relates to methods for treating infection as well as the inflammatory state associated with degenerative disc disease and chronic lower back pain.

BACKGROUND

Chronic low back pain (CLBP) is a leading cause of disability and hospitalization. Although many conditions lead to CLBP, degenerative disc disease (DDD) is among the most common diagnoses. Because correlations among clinical symptoms, radiological signs of disc degeneration, and treatment outcomes are not satisfactory, a more detailed understanding of the mechanisms of DDD and CLBP are needed to enable more effective treatment outcomes.

SUMMARY OF THE INVENTION

In various aspects and embodiments, the invention provides methods for treating degenerative disc disease or chronic lower back pain. The method comprises administering to a patient having degenerative disc disease or chronic lower back pain, and suspected of having a low-virulence infection (such as a *P. acnes* infection), an antibiotic and one or more of an IL-1β inhibitor and an inhibitor of Nerve Growth Factor (NGF). In various embodiments, the method alleviates or ameliorates the infective and inflammatory state that causes or exacerbates the patient's condition.

In some embodiments, the patient has chronic low back pain, and which is consistent with structural intervertebral disc damage and/or consistent with a low-virulence infection. Patients that have a low-virulence infection may be at increased risk of developing CLBP and/or may become "failed back surgery" patients, unless diagnosed correctly and treated appropriately. In accordance with this disclosure, *P. acnes* is believed to significantly amplify etiological factors that contribute to degenerate disc disease (DDD) through the expression of virulence factors and promotion of IL-1β and NGF, among others.

In some embodiments, the methods comprise detection or quantification of *Propionibacterium acnes* (*P. acnes*) in patient samples, or other commensal bacteria associated with low-virulence infection. In some embodiments, the patient has intervertebral disc disease or CLBP and a fine needle biopsy is isolated for testing. In these embodiments, the invention involves analysis of disc tissue for the presence of one or more commensal pathogens (e.g., *P. acnes*) or associated virulence factors or metabolites. In some embodiments, the presence of infection is determined using disc tissue following discectomy.

In some embodiments, the invention involves detecting or quantifying commensal pathogen(s) (e.g., *P. acnes*) in the disc tissue sample by microbiological cultivation and/or or by genetic, microbial-specific stain, immunochemical, or spectroscopic analysis. In some embodiments, the invention further comprises evaluating RNA from a disc tissue sample (e.g., mRNA or miRNA) to classify the profile as being indicative of low virulence infection, or not being indicative of a low virulence infection. In some embodiments, an RNA profile is evaluated independently to determine the presence of a low virulence infection, with or without the use of other techniques such as PCR, culture, or microscopy. In still other embodiments, the presence of the low-virulence infection is determined in a non-invasive manner, for example, by testing for an MR-spectroscopy signature. Non-invasive methods obviate the need for biopsy or disc tissue samples.

In still other embodiments, treatment is provided post-surgery to facilitate recovery and avoid recurrence. In such embodiments, disc tissue following discectomy is available for determining the likelihood that the patient is suffering from a chronic infection of the intervertebral disc. In cases where a low-virulence infection is not confirmed, the patient is not treated for a chronic infection.

Once infection has been established, therapeutic approaches combining appropriate antibiotic treatment with a therapy or therapies targeting IL 10 and/or NGF and/or anti-angiogenic therapy (concomitantly or sequentially) are undertaken.

Antibiotics can be administered locally to the intervertebral disc region, or administered systemically. In some embodiments, antibiotics (alone or with other therapies) are applied locally during a biopsy procedure. Exemplary antibiotics for *P. acnes* infection include clindamycin and erythromycin. In some embodiments, the antibiotic is a beta-lactam antibiotic, macrolide, or tetracycline. In some embodiments, a beta-lactam antibiotic is administered with a beta-lactamase inhibitor (e.g., clavulanate). The patient in some embodiments receives chronic antibiotic therapy, for example, for at least about 1 month, or at least about 2 months, or at least about 3 months (e.g., about 100 days or more).

In various embodiments, the patient further receives therapy with an IL-1β inhibitor. Exemplary IL-1β inhibitors include monoclonal antibodies against IL-1β antibody or fragment thereof, a recombinant protein with IL-1β binding activity, or a small molecule inhibitor. In some embodiments, the IL-1β inhibitor comprises a neutralizing or blocking antibody against IL-1β, a rIL-1RA, or an extracellular portion of the human IL-1R1 and/or IL-1 receptor accessory protein (IL-1RAcP). In still other embodiments, the IL-1β inhibitor is a caspase inhibitor (which prevents processing of proIL-1β), In some embodiments, the patient receives therapy with an inhibitor of Nerve Growth Factor (NGF), which can be provided with antibiotic treatment, or in combination with antibiotic treatment and IL-1β inhibitor therapy. In some embodiments, the NGF inhibitor is selected from a monoclonal anti-NGF antibody or fragment thereof, small-peptide mimetics of NGF, small-molecule TrkA antagonist, TrkA immunoadhesion molecule, soluble binding domain of NGF receptor, or monoclonal antibody or monoclonal antibody fragment against TrkA.

In some embodiments, the patient receives therapy with an anti-angiogenic therapy, such as a VEGF inhibitor, which can be provided with antibiotic treatment, or in combination with antibiotic treatment, IL-1β inhibitor therapy, and/or NGF therapy. In some embodiments, the angiogenesis inhibitor is selected from a monoclonal anti-VEGF antibody or fragment thereof, small-peptide mimetics, small-molecule antagonist (e.g., tyrosine kinase inhibitor), or soluble binding domain of VEGF receptor. Various other anti-angiogenic treatments are well known.

Dosage forms suitable for parenteral administration (e.g. intravenous, intramuscular, intraperitoneal, subcutaneous and intra-articular injection and infusion) include, for example, solutions, suspensions, dispersions, emulsions, and the like. They may also be manufactured in the form of sterile solid compositions (e.g. lyophilized composition), which can be dissolved or suspended in sterile injectable medium immediately before use.

Embodiments of the invention will be further illustrated with the following non-limiting examples.

ABBREVIATIONS

Figure 1:
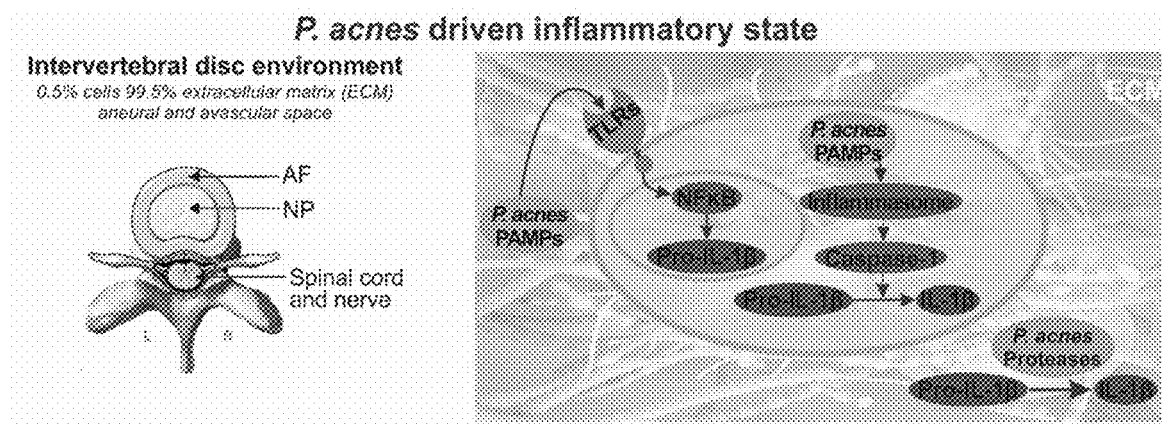
FIG. 1 illustrates a *P. acnes*-driven inflammatory state. *P. acnes* PAMPs bind to TLRs, which activate NF-κB, leading to the synthesis of pro-IL-1β; *P. acnes* PAMPs also activate inflammasomes (NLRP3) and caspase-1, which convert pro-IL-1β to IL-1β; *P. acnes* proteases directly convert pro-IL-1β to IL-1β.
Figure 2:
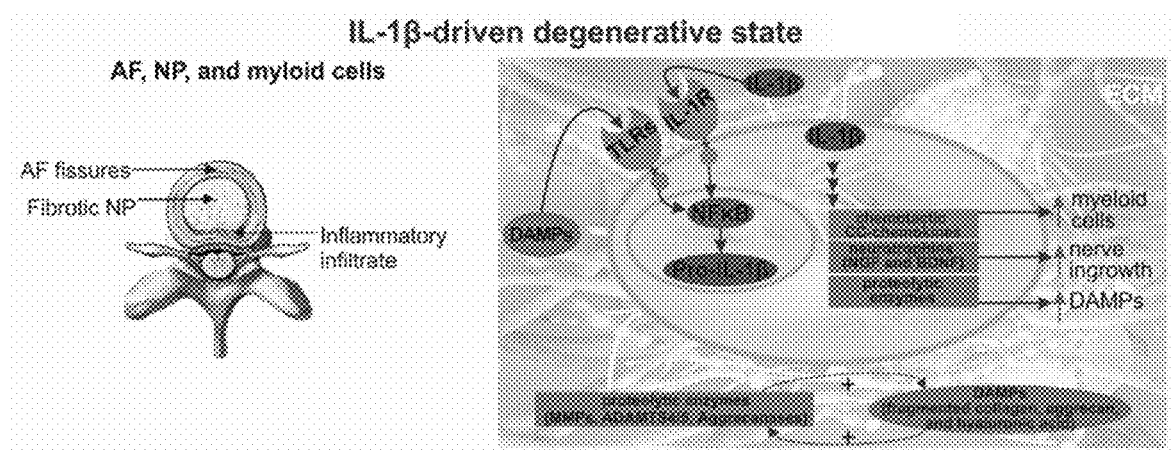
FIG. 2 illustrates an IL-1β driven degenerative state. IL-1β stimulates production of CC-chemokines that recruit myeloid cells, neurotrophins NGF and BDNF that induce nerve ingrowth, and proteolytic enzymes (MMPs, ADAMTS4/5 aggrecanases) that degrade the ECM. Positive feedback loops arise when IL-1β binds to IL-1R and when extracellular matrix degradation products (DAMPs; e.g. fragmented collagen, aggrecan, and hyaluronic acid) activate TLRs. Both binding events further stimulate IL-1β production.
Figure 3:
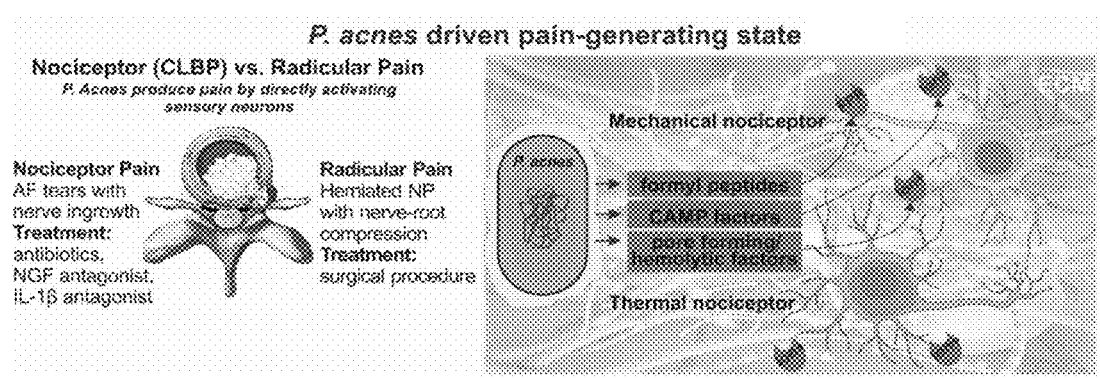
FIG. 3 illustrates a *P. acnes* driven, pain generating state. *P. acnes* directly activates nociceptors through several distinct mechanisms: N-formylated peptides activate FPR on a subset of nociceptor neurons that mediate mechanical hyperalgesia; CAMPs and pore-forming hemolytic factors allow the entry of ions that lead to depolarization that induces mechanical and thermal hyperalgesia.

ADAMTS-4/5, a disintegrin and metalloproteinase with thrombospondin motifs 4/5; AF, anullus fibrosus; BDNF, brain-derived neurotrophic factor; CAMP, Christie, Atkins and Munch-Petersen factors; CLBP, chronic low back pain; DAMPs, damage-associated molecular patterns; DDD, degenerative disc disease; ECM, extracellular matrix; PAMPs, pathogen-associated molecular patterns; FPR, N-formylated peptide receptor; IL-1R, interleukin-1 receptor; MMPs, matrix metalloproteinases; NF-κB, nuclear factor KB; NGF, nerve growth factor; NP, nucleus pulposus; TLRs, Toll-like receptors, MOI, multiplicity of infection.

DETAILED DESCRIPTION

In various aspects and embodiments, the invention provides methods for treating degenerative disc disease or chronic lower back pain. The method comprises administering to a patient having degenerative disc disease or chronic lower back pain, and suspected of having a low-virulence infection, an antibiotic and one or more of an IL-1β inhibitor, an inhibitor of Nerve Growth Factor (NGF), and an anti-angiogenic therapy. In various embodiments, the method alleviates or ameliorates the infective and inflammatory state that causes or exacerbates the patient's condition. In various embodiments, the method can be employed with or without surgical interventions to resolve both radicular pain and nociceptor pain that may be associated with the condition.

As the term is used herein, a low-virulence infection is a chronic, low-grade, infection that is associated with a commensal microorganism. Exemplary commensal microorganisms include without limitation, *Propionibacterium* sp. (*P. acnes*) *Staphylococcus* sp. (e.g., coagulase negative *staphylococcus*, or *Staphylococcus aureus* or *Staphylococcus epidermidis*), *Corynebacterium, Lactobacillus* sp., *Pseudomonas* sp. (e.g., *Pseudomonas aeruginosa*), *Enterococcus* sp., *Streptococcus* sp. (e.g., *S. pneumoniae*), *Bacillus* sp. (e.g., *Bacillus cereus*), *Citrobacter* sp., *E. coli, Moraxella* sp., *Haemophilus* sp., *Neisseria* sp., *Clostridium* sp., *Enterobacter* sp., and *Klebsiella* sp. In some embodiments, the microorganism has a biofilm forming phenotype.

In some embodiments, the patient has chronic low back pain, and which is consistent with structural intervertebral disc damage and/or a low-virulence infection. In some embodiments, the patient may be a candidate for, and may be scheduled for, intervertebral disc surgery. Patients that have a low-virulence infection may be at increased risk of developing CLBP and/or may become "failed back surgery" patients, unless diagnosed correctly and treated appropriately. For example, some patients that undergo disc surgery will also suffer from CLBP prior to the acute condition necessitating their surgery. Also, a certain proportion (around 5 to 10%) of patients undergoing disc surgery will develop CLBP in the follow-up, which are sometimes referred to as "failed back surgery" patients or "post-discectomy syndrome". These conditions are statistically associated with a low-virulence infection.

Stirling et al. (2001) published the first evidence of bacterial infection of the degenerated disc in 2001. Stirling et al. found that 19 of 36 (53%) sciatica patients who had undergone microdiscectomy tested positive for bacterial infection; 84% of these were *Propionibacterium acnes* (*P. acnes*) infections. Subsequent research yielded conflicting results, but two independent meta analyses (Urquhart 2015; Ganko 2015) reported the pooled prevalence of bacterial infection was 34% or 36.2% and *P. acnes* was identified as the major infecting species. They found moderate evidence that low virulent bacteria play a role in disc degeneration and moderate evidence of causation, but indicated that these observations could result from bacterial contamination. A more recent 368-patient study (Capoor 2017) confirmed the previously observed prevalence and found that *P. acnes* was the only significant species isolated from degenerated disc tissue. Importantly, this study documented the presence of *P. acnes* biofilm in the infected disc tissue; a result consistent with infection rather than perioperative contamination.

While antibiotic therapy has seen some moderate results in the treatment of CLBP, in accordance with this disclosure, it is believed that antibiotic therapy alone may not be effective to relieve the chronic inflammatory state, particularly of damaged intervertebral discs, which is susceptible to recurrent infection by *P. acnes*. Further, some patients will not have a low virulence infection, and thus should not be unnecessarily treated with antibiotics.

*P. acnes* plays a key role in the development of acne vulgaris, as well as roles in other chronic and recurrent infections, including implant infections, which are facilitated by the organism's ability to form biofilms. In pilosebaceous units, *P. acnes* pathogen-associated molecular patterns (PAMPs) bind to toll-like receptor (TLR) 2 on sebocytes. This activates NF-κB signaling and results in the production of pro-IL-1β. *P. acnes* PAMPs also trigger NLRP3 inflammasome activation, which facilitates pro-IL-1β cleavage and the excessive release of mature IL-1β. IL-1β promotes dermal matrix destruction through induction of matrix metalloproteases (MMPs). Progression of the inflammation results in follicular rupture, allowing *P. acnes* to leak out of the pilosebaceous unit and activate perifollicular myeloid cells. This results in further release of IL-1β and neutrophil-rich perifollicular inflammation. Thus, IL-1β is the driver of inflammatory responses to *P. acnes* in acne vulgaris.

Disc degeneration is known to be mediated by the abnormal secretion of cytokines by the inner nucleus pulposus (NP) and outer annulus fibrosus (AF) cells of the intervertebral disc, as well as by immune cells attracted to the site of disc degeneration. The initiating insult is thought to trigger NF-κB signaling through TLRs and stimulate the production of pro-IL-1β. Increased levels of NLRP3 and caspase-1 have also been described in degenerated disc tissue, indicating inflammasome activation and facilitated maturation of pro-IL-1β. In addition, *P. acnes* proteases have been found to convert pro-IL-1β to mature IL-1β. Inflammatory actions are further amplified because IL-1β is not only an NF-κB target gene, but also an NF-κB activator, forming a positive feedback loop. This IL-1β-IL-R1 signaling promotes extracellular matrix degradation through induction of proteolytic enzymes, including MMPs 1, 2, 3, 9, and 13 and aggrecanases of 'a disintegrin and metalloproteinase with thrombospondin motifs (ADAMTS) families 4/5. Specific damage-associated molecular patterns (DAMPs), which include fragmented collagen, aggrecan, or hyaluronic acid, bind to TLRs on NP and AF cells and activate NF-κB, forming another positive feedback loop. IL-1β also promotes the production of chemotactic CC-chemokines, mainly CCL3 and CCL4, leading to the recruitment and activation of infiltrating immune cells that further amplify the inflammatory cascade. These pathways form the core of a model in which *P. acnes* infection causes IL-1β release by NP, AF and immune cells, which leads to extracellular matrix degradation within the intervertebral disc.

The ingrowth of nociceptive nerve fibers into the degenerated disc, usually accompanied by the presence of annular fissures can be a main source of nociception related to CLBP. IL-1β has been shown to induce the expression of neurotrophin-like nerve growth factor (NGF) and brain-derived neurotrophic factor (BDNF) in both disc and immune cells, supporting nerve ingrowth into the degenerated disc. IL-1β-stimulated NGF and BDNF production further induces expression of pain-associated cation channels in the dorsal root ganglion, the depolarization of which is likely to promote low back and radicular pain. Finally, NGF has a direct activating or sensitizing effect on nociceptors, and its upregulation in CLBP has been demonstrated.

Disc cells (NP and AF) make up a small portion of the disc tissue mass and primarily remove waste and receive nutrition through diffusion. In degenerative disc disease, there can be nerve ingrowth and likely some level of angiogenesis to support the nerve ingrowth. In accordance with this disclosure, *P. acnes* produces alpha-hemolysins and other virulence factors that interact with nociceptors in nerve in-growths, resulting in CLBP. Further, in accordance with this disclosure, *P. acnes* is believed to significantly amplify etiological factors that contribute to degenerate disc disease (DDD) through the promotion of IL-1β and facilitates pathogenesis in synergy with other etiological factors of DDD.

Since activation of IL-1β system promotes low back pain, *P. acnes* as extensive inducer of IL-1β indirectly participates in the pathogenesis of CLBP. Based on the ability of *Staphylococcus aureus* to activate sensory neurons by releasing formyl peptides and the pore-forming/hemolytic virulence factor α-haemolysin, it is believed that there is also a direct, IL-1β independent, mechanism of *P. acnes* involvement in CLBP realized through the release of pore-forming hemolysins that induce calcium flux and action potentials in nociceptive neurons. This is supported by the fact, that *P. acnes* genome contains several putative pore-forming/hemolytic virulence factors (e.g. genes PPA687, PPA1198, PPA1231, PPA1340, and PPA2108 encoding homologs of Christie, Atkins and Munch-Petersen (CAMP) factors, potentially hemolytic gene products including PPA565, which shares similarity with hemolysin III of *B. cereus*, and PA938 (COG1253) and PPA1396 (COG1189), which share similarity with the hemolysins TlyC and TlyA of *Brachyspira hyodysenteriae*, respectively). These hemolytic factors are clinically relevant, as hemolysis can be used as a clinical marker for the presence of *P. acnes* in orthopedic infections. Therefore, *P. acnes* can play a role in the pathogenesis of CLBP, and *P. acnes* bacterial load could be directly linked to clinical course of CLBP.

In some embodiments, the methods comprise detection or quantification of *Propionibacterium acnes* (*P. acnes*) or infection thereof in patient samples, or infection by other commensal bacteria associated with low-virulence infection. *P. acnes* is a gram-positive aerotolerant anaerobe that forms part of the normal resident microbiota of the skin, oral cavity and the gastrointestinal and genito-urinary tracts. It is an opportunistic pathogen that has been linked to a wide range of infections and conditions, including implant infections, discitis, musculoskeletal conditions (e.g., osteitis, osteomyelitis, synovitis-acne-pustulosis-hyperostosis-osteitis (SAPHO) syndrome), sarcoidosis, chronic prostatitis, and prostate cancer.

Thus, in some embodiments, the patient has intervertebral disc disease or CLBP and a fine needle biopsy is isolated for testing. In these embodiments, the invention involves analysis of disc tissue for the presence of infection of one or more commensal pathogens (e.g., *P. acnes*), and/or for the presence of an RNA signature indicative of a low-virulence infection. In some embodiments, the presence of infection is determined using disc tissue following discectomy.

In some embodiments, the invention involves detecting or quantifying commensal pathogen(s) (e.g., *P acnes*) in the disc tissue sample by microbiological cultivation or by genetic, microbial-specific stain, immunochemical, or spectroscopic analysis. In some embodiments, the invention further comprises evaluating the RNA from a sample (e.g., mRNA or miRNA) to classify the profile as being indicative of low virulence infection, or not being indicative of a low virulence infection. In some embodiments, an RNA profile is evaluated independently to determine the presence of a low virulence infection, with or without the use of other techniques such as PCR, culture, or microscopy.

In some embodiments, an RNA profile (of host tissue) is evaluated for the presence of an RNA signature (e.g., mRNA or miRNA signature) that is indicative of a low-grade or low-virulence infection. Exemplary RNA signatures are disclosed in WO 2017/019440, which is hereby incorporated by reference. An exemplary miRNA score for *P. acnes* infection can be determined by scoring the relative expression levels of miR-29a-3p and miR-574-3p. For example, a diagnostic miRNA score (DMS) based on the following formula results in high specificity using a cut-off of −0.3: DMS=18.71−11.24*log 10 (miR-29a-3p)+10.4*log 10 (miR-574-3p). Other RNA signatures can be trained from RNA profiles of samples that are positive or abundant for *P. acnes* (or other commensal microorganism) and samples that test negative (or non-abundant) for *P. acnes* (or other commensal microorganisms). For example, samples can be binned based on detection (or detection level) of *P. acnes* by quantitative PCR and at least one other technique, such microbial culture or spectroscopy (including with microbial stains, FISH, or immunohistochemistry).

In some embodiments, the presence of a low-virulent infection is evaluated by culture, including aerobic and/or anaerobic cultivation and subsequent biochemical and spectroscopic (e.g., mass spec., MALDI-TOF MS, or NMR) identification of species. For genetic analysis, nucleic acids (e.g., DNA and/or RNA) are isolated from the sample for analysis. In still other embodiments, immunochemistry (e.g., immunohistochemistry or ELISA) can be used to detect protein or other epitopes of commensal organisms. For instance, without limitation, monoclonal antibodies against *P. acnes* antigens including virulence factors can be used, such as antibodies specific for epitopes of cell-membrane-bound lipoteichoic acid (PAB antibody) and ribosome-bound trigger factor protein (TIG antibody). In some embodiments, antibodies specific for *P. acnes* alpha-hemolysin or formylated peptide is used to identify these virulence factors in biopsy or disc material, which indicates that the patient is suffering from a low virulence infection. Other techniques such as microscopy on tissue samples can be used to identify positive samples, and may employ any appropriate staining reagent (e.g., gram stain, *P. acnes*-specific stain, or fluorescent in situ hybridization (FISH)) or other immunoreagents specific for the commensal microorganism of interest. Mass spectroscopy techniques can be used to identify *P. acnes*-specific molecules that are indicative of infection, including biofilm components.

In some embodiments, the presence or level of commensal pathogens is determined (alternatively or in addition to culturing) by hybridization or amplification of microbial nucleic acids. For example, detection assays include real-time or endpoint polymerase chain reaction (PCR), nucleic acid hybridization to microarrays, or nucleic acid sequencing. In some embodiments, the molecular detection assay detects microbial ribosomal RNA (rRNA) genes, such as 16S and/or 23S rRNA genes, and particularly the variable regions of 16S. In some embodiments, the presence of a commensal pathogen is determined by a microarray hybridization-based assay. Exemplary methods for diagnosing a low-virulence infection of an intervertebral disc are described in WO 2017/019440, which is incorporated herein by reference.

In some embodiments, the presence of the low-virulence infection is determined in a non-invasive manner. For example, in some embodiments an MR-spectroscopy signature is obtained to determine the chemical composition of the intervertebral disc. The chemical composition may comprise biofilm components specific for *P. acnes* biofilm, as well as other molecules indicative of *P. acnes* infection. Exemplary methods for performing MRS on intervertebral discs are described in US 2011/0087087, which is hereby incorporated by reference in its entirety.

In some embodiments of the present invention, where the diagnostic test confirms a low-virulence infection, the patient is treated for infection before any invasive surgery (such as discectomy), and in some embodiments, invasive procedures may be entirely avoided.

In still other embodiments, treatment is provided post-surgery to facilitate recovery and avoid recurrence. In such embodiments, disc tissue following discectomy is available for determining the likelihood that the patient is suffering from a chronic infection of the intervertebral disc. In cases where a low-virulence infection is not confirmed, the patient is not treated for a chronic infection.

Antibiotic treatment consisting of amoxicillin (500 mg)-clavulanic acid (125 mg) three times a day for 100 days has been used in patients with CLBP unresponsive to conservative therapies with mixed results. [Albert 2013; Palazzo 2017] However, the patient populations in these studies were not evaluated for the presence of infection or IL-1β overexpression prior to treatment; the treatment provided was not typical of the antibiotic regimens normally used to treat *P. acnes* infection (Jahns 2016; Zeller 2007); and even if *P. acnes* infection were to be successfully eradicated, other etiological factors could support ongoing IL-1β-based inflammatory process and NGF-dependent nerve ingrowth and nociception, leading to treatment failure.

Once infection has been established, therapeutic approaches combining appropriate antibiotic treatment with a therapy or therapies targeting IL-1β and/or NGF and/or angiogenesis (concomitantly or sequentially) are undertaken. A range of therapies targeting these factors are available, including several monoclonal antibody therapies. Development of an appropriate diagnostic strategy will rationalize indication of the combination therapy and a provide path to precision medicine in the treatment of DDD and CLBP.

Antibiotics can be administered locally to the intervertebral disc region (e.g., by injection or transdermally), or administered systemically (e.g., orally or i.v.). In some embodiments, antibiotics (alone or with other therapies) are applied locally during a biopsy procedure. Exemplary antibiotics for *P. acnes* infection include clindamycin and erythromycin. In some embodiments, the antibiotic is a tetracycline antibiotic, such as tetracycline, minocycline, doxycycline, oxytetracycline and lymecycline. In various embodiments, depending on the etiology of the infection, the antibiotic can be a beta-lactam antibiotic, macrolide, or tetracycline. For example, the antibiotic is selected from benzylpenicillin, amoxicillin, ampicillin, dicloxacillin, methicillin, nafcillin, oxacillin, penicillin G, cephalexin, cefoxitin, cephalolothin, ceftriaxone, ciprofloxacin, chloramphenicol, erythromycin, tetracycline, vancomycin, clindamycin, fusidic acid, doxycycline, moxifloxacin, linezolid, rifampicin, ertapenem, taurolidine, or a combination thereof. In some embodiments, a beta-lactam antibiotic (such as amoxicillin) is administered with a beta-lactamase inhibitor (e.g., clavulanate). The antibiotic given orally are generally selected from those that are able to penetrate the intervertebral disc.

The patient in some embodiments receives chronic antibiotic therapy, for example, for at least about 1 month, or at least about 2 months, or at least about 3 months (e.g., about 100 days or more).

In various embodiments, the patient further receives therapy with an IL-1β inhibitor. Exemplary IL-1β inhibitors include monoclonal antibodies against IL-1β antibody or fragment thereof, a recombinant protein with IL-1β binding activity, or a small molecule inhibitor. Exemplary antibody fragments include single chain variable fragments. In some embodiments, the IL-1β inhibitor comprises a neutralizing or blocking antibody against IL-1β, a rIL-1RA, or an extracellular portion of the human IL-1R1 and/or IL-1 receptor accessory protein (IL-1RAcP), which can be linked in-line to IgG Fc region. In still other embodiments, the IL-1β inhibitor is a caspase inhibitor (or other inhibitor that prevents processing of proIL-1β), and which is optionally administered orally.

Exemplary IL-1β inhibitors are selected from anakinra, rilonacept, canakinumab, geviokizumab, LY2189102, MED-8968, CYT013, sIL-1RI, sIL-1RII, EBI-005, CMPX-1023, VX-765 (Pralnacasan), IL-1trap, CDP-484, CP424174, CP412245, CJ14877, CJ14897, and LL-Z1271a.

The IL-1β antagonist or inhibitor can be administered by a route selected from parenteral, oral, and transdermal. Generally, where the inhibitor is a biologic, such as an antibody or portion thereof or other recombinant protein, the inhibitor may be administered parenterally, including subcutaneous injection, intramuscular injection, intravenous injection, or local injection to intervertebral disc tissue. In some embodiments, the therapy is provided during a biopsy procedure. In some embodiments, the IL-1β inhibitor is a small molecule (such as caspase inhibitor), and may be administered orally or transdermally in some embodiments.

In some embodiments, the therapy with the IL-1β inhibitor is concurrent with antibiotic therapy (e.g., for at least about 1 month, 2 months, or 3 months) or is administered after antibiotic therapy. In some embodiments, the course of therapy with the IL-1β inhibitor is shorter or longer than antibiotic therapy, such as about 2 weeks, about 3 weeks, about 1 month, about 2 months, about 3 months, or for 6 months or more. Administrations may be given daily, weekly, or every other week, or monthly. Generally, biologics are administered weekly, every other week, or monthly. In some embodiments, the patient receives from 2 to 8 doses of IL-1β inhibitor.

In some embodiments, the patient receives therapy with an inhibitor of Nerve Growth Factor (NGF), which can be provided with antibiotic treatment, or in combination with antibiotic treatment and IL-1β inhibitor therapy. In some embodiments, the NGF inhibitor is selected from a monoclonal anti-NGF antibody or fragment thereof (including a scvf), small-peptide mimetics of NGF, small-molecule TrkA antagonist, TrkA immunoadhesion molecule, soluble binding domain of NGF receptor, or monoclonal antibody or monoclonal antibody fragment against TrkA. Tropomyosin receptor kinase A (TrkA) is also known as high affinity nerve growth factor receptor. In some embodiments, the inhibitor of NGF is tanezumab, fulranumab, TrkAd5, AMG 403, Appha-D11, MNAC13, ALE0540, PD90780, or PPC-1807.

The NGF inhibitor can be administered by a route selected from parenteral, oral, and transdermal, and in some embodiments is administered during a biopsy procedure. Generally, where the inhibitor is a biologic, such as an antibody or portion thereof or other recombinant protein, the inhibitor may be administered parenterally, including subcutaneous injection, intramuscular injection, intravenous injection, or local injection to intervertebral disc tissue. In some embodiments, the NGF inhibitor is a small molecule, and may be administered orally or transdermally in some embodiments.

In some embodiments, the therapy with the NGF inhibitor is concurrent with antibiotic therapy (e.g., for at least about 1 month, 2 months, or 3 months) or is administered after antibiotic therapy. In some embodiments, the course of therapy with the NGF inhibitor is shorter or longer than antibiotic therapy, such as about 2 weeks, about 3 weeks, about 1 month, about 2 months, about 3 months, or for 6 months or more. Administrations may be given daily, weekly, or every other week, or monthly. Generally, biologics are administered weekly, every other week, or monthly. In some embodiments, the patient receives from 2 to 8 doses of IL-1β inhibitor. The NGF inhibitor therapy may be concurrent with IL-1β therapy, including separate or co-formulation.

In some embodiments, the patient receives an anti-angiogenic therapy, which can be provided with antibiotic treatment, or in combination with antibiotic treatment and IL-1β inhibitor therapy and/or anti-NGF therapy. In some embodiments, the angiogenesis inhibitor is a VEGF pathway inhibitor, which can be a monoclonal anti-VEGF antibody or fragment thereof (including a scvf), small-peptide mimetics, small-molecule inhibitor (e.g., tyrosine kinase inhibitor), or soluble binding domain of VEGF receptor. Exemplary angiogenesis inhibitors include antibodies directed against VEGF or VEGFR, soluble VEGFR/VEGFR hybrids, and tyrosine kinase inhibitors. An exemplary VEGF pathway inhibitor is Bevacizumab. Bevacizumab binds to VEGF and inhibits it from binding to VEGF receptors.

The angiogenesis inhibitor can be administered by a route selected from parenteral, oral, and transdermal, and in some embodiments is administered during a biopsy procedure. Generally, where the inhibitor is a biologic, such as an antibody or portion thereof or other recombinant protein, the inhibitor may be administered parenterally, including subcutaneous injection, intramuscular injection, intravenous injection, or local injection to intervertebral disc tissue. In some embodiments, the angiogenesis inhibitor is a small molecule, and may be administered orally or transdermally in some embodiments.

In some embodiments, the therapy with the angiogenesis inhibitor is concurrent with antibiotic therapy (e.g., for at least about 1 month, 2 months, or 3 months) or is administered after antibiotic therapy. In some embodiments, the course of therapy with the angiogenesis inhibitor is shorter or longer than antibiotic therapy, such as about 2 weeks, about 3 weeks, about 1 month, about 2 months, about 3 months, or for 6 months or more. Administrations may be given daily, weekly, or every other week, or monthly. Generally, biologics are administered weekly, every other week, or monthly. In some embodiments, In some embodiments, the patient receives from 2 to 8 doses of IL-1β inhibitor. The angiogenesis inhibitor therapy may be concurrent with IL-1β therapy, including separate or co-formulation.

Dosage forms suitable for parenteral administration (e.g. intravenous, intramuscular, intraperitoneal, subcutaneous and intra-articular injection and infusion) include, for example, solutions, suspensions, dispersions, emulsions, and the like. They may also be manufactured in the form of sterile solid compositions (e.g. lyophilized composition), which can be dissolved or suspended in sterile injectable medium immediately before use. They may contain, for example, suspending or dispersing agents known in the art. Formulation components suitable for parenteral administration include a sterile diluent such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as EDTA; buffers such as acetates, citrates or phosphates; and agents for the adjustment of tonicity such as sodium chloride or dextrose.

For intravenous administration, suitable carriers include physiological saline, bacteriostatic water, Cremophor EL™ or phosphate buffered saline (PBS). The carrier should be stable under the conditions of manufacture and storage, and should be preserved against microorganisms. The carrier can be a solvent or dispersion medium containing, for example, water, ethanol, polyol (for example, glycerol, propylene glycol, and liquid polyethylene glycol), and suitable mixtures thereof.

Embodiments of the invention will be further illustrated with the following non-limiting examples.

EXAMPLES

Example 1. Ability of P. acnes to Induce IL-1β-Based Pathogenesis

The ability of P. acnes PAMPs to induce IL-1β and trigger NLRP3 inflammasome assembly are demonstrated by monitoring of IL-1β, NLRP3 and caspase 1 levels in ex vivo models based on NP and AF cell cultures derived from clinical specimens of degenerated disc tissue. In vivo models in which animals are experimentally infected with P. acnes strains isolated from human degenerated discs could also be employed. Further, short fragments of hyaluronic acid, P. acnes-induced DAMPs, shown to interact with TLR2 of the NP cells in vitro, could also be confirmed to induce IL-1β in an animal experiment.

To further establish that P. acnes is a strong contributor to IL-1β-based pathogenesis of DDD, in vitro and in vivo experiments are performed to quantitatively compare the ability of P. acnes to induce IL-1β with other known activators of IL-1β used in the experimental studies of DDD. Ability of the P. acnes related formyl peptides and the pore-forming/hemolytic virulence factor to induce calcium flux and action potentials in nociceptive neurons could be evaluated in vitro using analogical designs as used in study of Staphylococcus aureus.[19]

Expression levels of pro-inflammatory cytokines and nerve growth factors were assessed in P. acnes-infected cell cultures derived from human tissue samples of degenerated nucleus pulposus (NP).

Eight NP cell primary cultures were established from human tissue samples of degenerated nucleus pulposus (NP) that were obtained from eight patients who underwent microdiscectomy for lumbar disc herniation. Further, a P. acnes strain (type II) derived from P. acnes strongly positive herniated disc tissue was used for in vitro infection of NP cells disc cultures.

Figure 4:
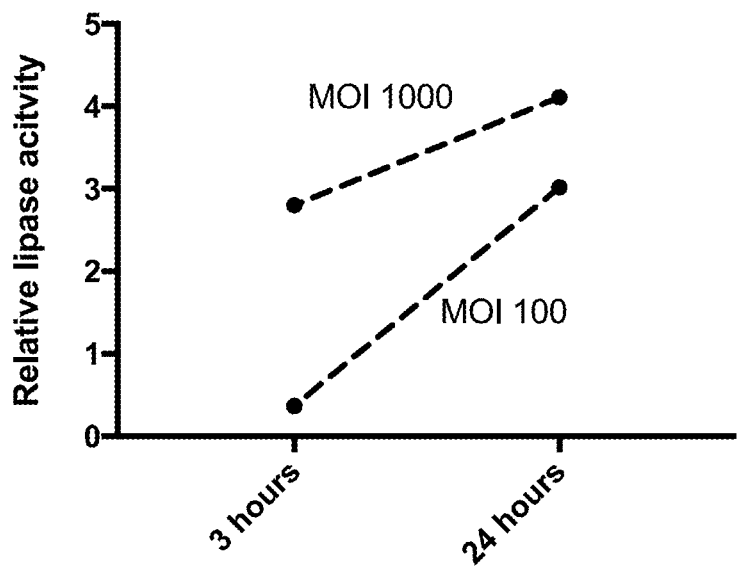
FIG. 4 depicts relative lipase activity after 3 h and 24 h of 1:100 and 1:1000 NP cells/*P. acnes* co-cultures, confirming viability of *P. acnes*.
Figure 5:
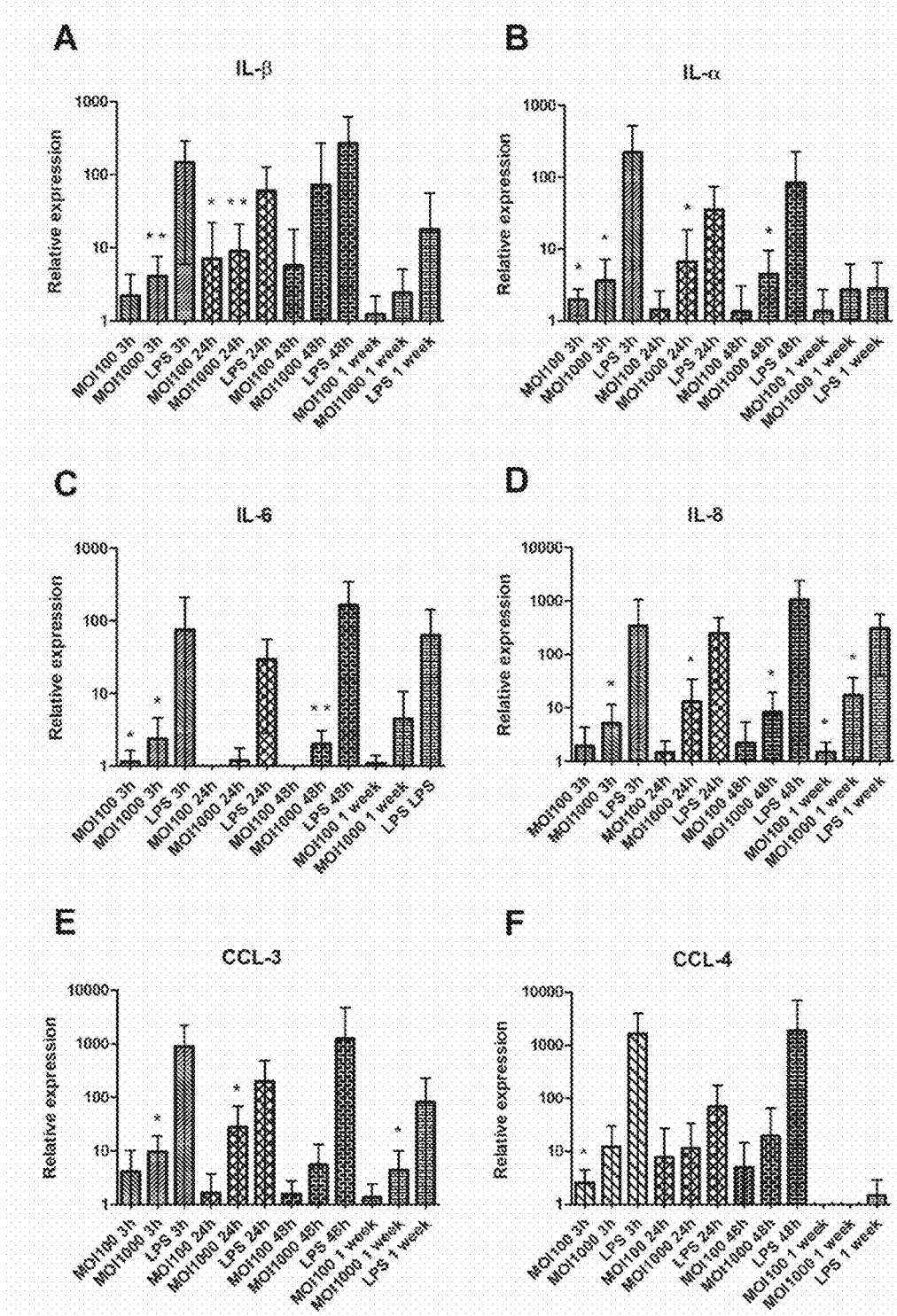
FIG. 5 depicts average expression levels of pro-inflammatory cytokines (IL-113, IL-1α, IL-6, IL-8, CCL3, CCL4) at four time-points (3 h, 24 h, 48 h and 1 week) and MOI100 and MOI1000 normalized to their levels in non-infected NP cells. LPS-treated cells were used as positive controls ($*P<0.05$, $**P<0.01$).

Experiments were performed in triplicates with two multiplicities of infection (MOI), e.g., 100, 1000, and expression levels of pro-inflammatory cytokines (e.g., IL-1β, IL-1α, IL-6, IL-8, CCL3, CCL4) and nerve growth factors (e.g., NGF, BDNF) were quantified by quantitative real-time PCR at four time-points (3 h, 24 h, 48 h and 1 week). Non-infected cells were used as negative controls and LPS-treated cells were used as positive controls. FIG. 4 depicts the presence of viable P. acnes strain in the NP culture, as confirmed by P. acnes lipase assay. Specifically, relative lipase activity of 1:100 and 1:1000 NP cells/P. acnes co-cultures was assayed after 3 hours and 24 hours, confirming the viability of P. acnes. FIG. 5 shows the average expression levels of the tested genes: IL-1β, IL-1α, IL-6, IL-8, CCL3, and CCL4. The data shows significant increase in expression of all tested cytokines with the most significant changes observed after 24 hours and MOI 1000.

On the other hand, when the expression changes of the cytokines were evaluated at the level of the individual NP cell cultures, it was obvious that the dynamics of the inflammatory response differed between the cell cultures. For example, fold changes related to IL-1β presented across various cell lines and under different conditions are summarized in Table 1 below:

TABLE 1

IL-1β expression changes in various cell lines and under different conditions
(+, fold-change > 1 < 2; ++, fold-change > 2 < 5; +++, fold-change > 5).

|  | MOI100 3 h | MOI1000 3 h | MOI100 24 h | MOI1000 24 h | MOI100 48 h | MOI1000 48 h | MOI100 1 w | MOI1000 1 w |
|---|---|---|---|---|---|---|---|---|
| KB7007 | + | ++ | − | +++ | + | + | + | − |
| RT7806 | + | ++ | + | +++ | − | − | − | + |
| MP7910 | +++ | +++ | +++ | +++ | +++ | +++ | − | + |
| ML7364 | +++ | +++ | + | ++ | + | ++ | − | − |
| SM7859 | ++ | ++ | − | + | − | ++ | − | − |
| JP8161 | − | − | − | ++ | − | − | ++ | +++ |
| VC5509 | − | − | ++ | + | ++ | +++ | + | ++ |
| MH6257 | − | − | +++ | +++ | − | ++ | − | − |

In some cases, an observed cytokine response did not present until after 24 hours.

Figure 6:
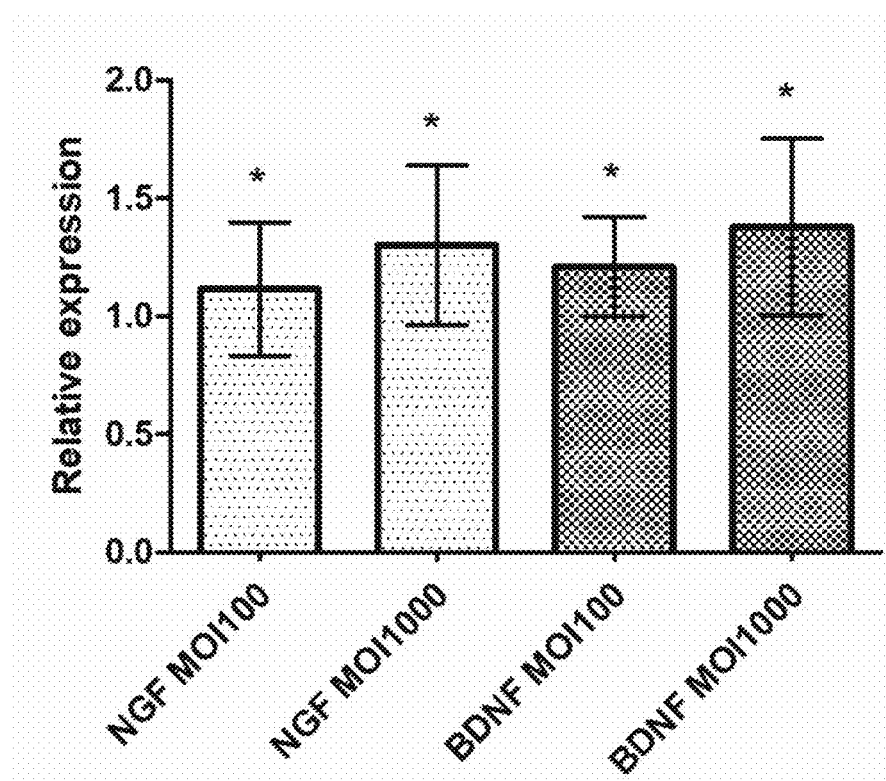
FIG. 6 illustrate an increase in the NGF and BDNF expression levels in *P. acnes*-infected NP cells after one week of infection ($*P<0.05$).
Figure 7:
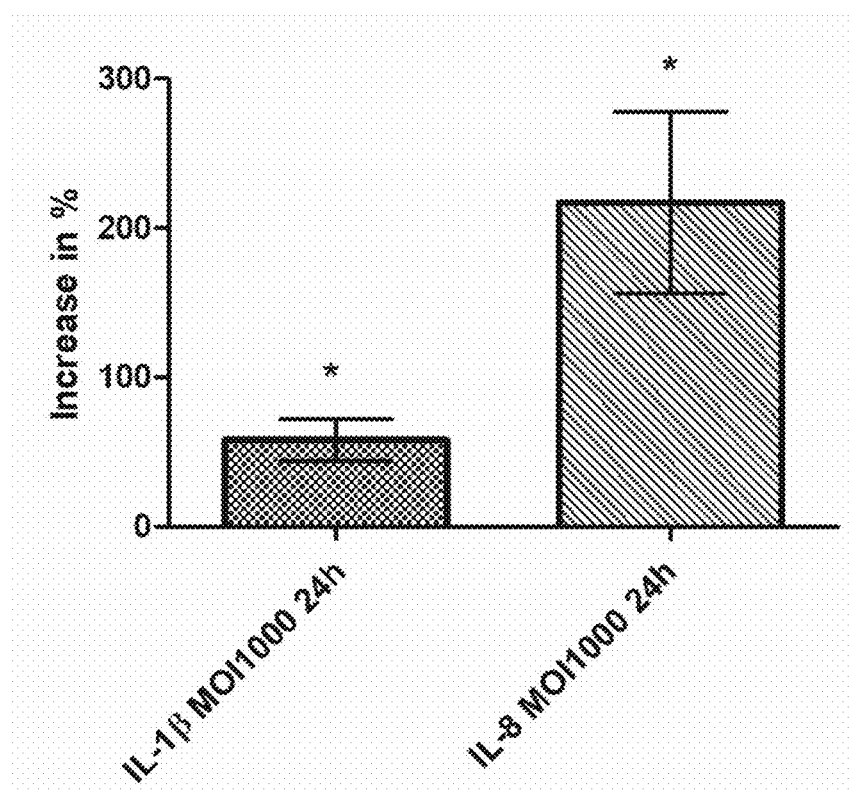
FIG. 7 shows an increase in IL-1β protein in NP cells after 24 hours of *P. acnes* infection, as detected by ELISA ($*P<0.05$).

The data further showed that no significant changes were found in NGF and BDNF expression levels after 3 h, 24 h and 48 hours of lasting infection. FIG. 6 depicts an MOI-dependent significant increase in NGF and BDNF expression levels in P. acnes-infected NP cells observed after one week of infection. In the case of the disc degeneration driving the cytokine IL-1β, FIG. 7 shows that its protein expression levels were also increased 24 hours post-infection, as detected by ELISA.

Since P. acnes is known to be sensitive to the antibiotic clindamycin in the therapy of acne vulgaris, this study further sought to assess the effect of clindamycin treatment in suppressing production and expression of pro-inflammatory cytokines in human NP cells induced by P. acnes.

Figure 8:
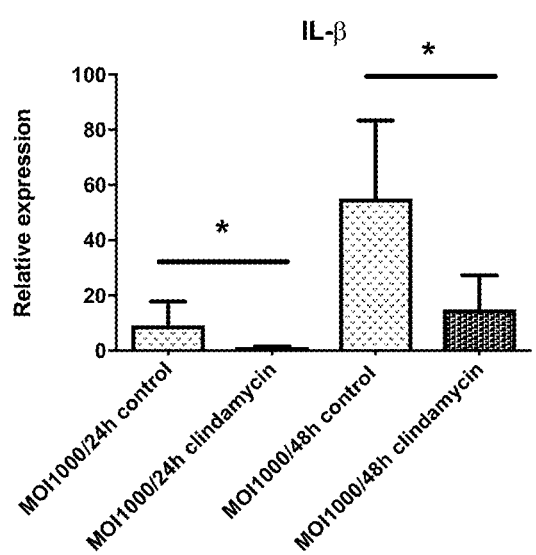
FIG. 8 depicts clindamycin suppression of the production of IL-1β, IL-6 and IL-8 in *P. acnes*-infected NP cells. Averages from the experiments with the three NP cell cultures are presented ($*P<0.05$, $**P<0.01$).
Figure 8:
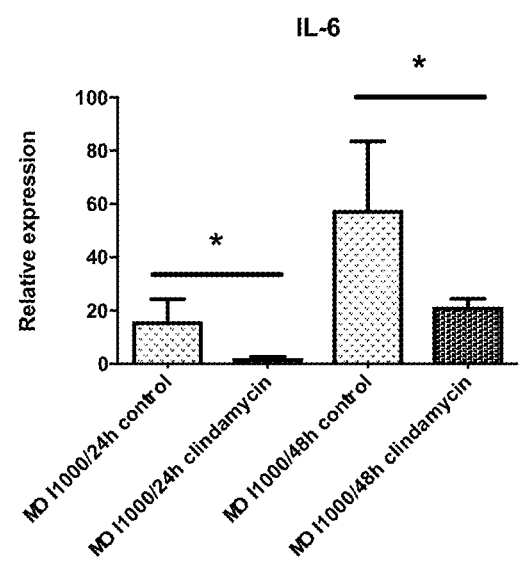
Figure 8:
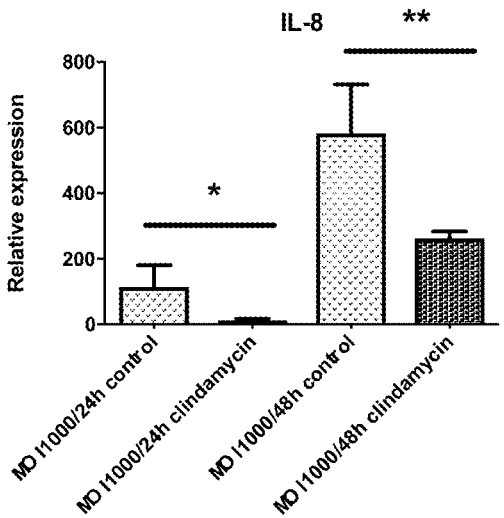

Accordingly, NP cell cultures derived from three specimens of clinical disc tissue were infected with one of the *P. acnes* strains (type II) derived from *P. acnes* strongly positive herniated disc tissues (MOI 1000). Half of the plates were treated with 0.25 g/mL clindamycin, and expression levels of IL-1β, IL-6 and IL-8 were measured after 24 hours and 48 hours. Significantly lower expression levels of all cytokines at both time points were observed, as shown in FIG. 8, indicating the ability of clindamycin to suppresses expression of pro-inflammatory cytokines in human NP cells induced by *P. acnes*.

Materials and Methods
Microbiological Culture

The disc fragment for culture was weighed, placed into a Micro Bag (Seward) containing 4 ml of Viande-Levure medium, and homogenized with a Stomacher 80 (Seward) under aseptic conditions. 100 µl of the resultant homogenate was inoculated onto Wilkins Chalgren Anaerobic Agar with 7% sheep's blood and vitamin K (Hi Media Laboratories). An Anaerobic Work Station Concept 400 (Ruskinn Technology) was utilized for culture; inoculated plates were incubated for 14 days at 37° C. with an atmosphere of 80% N2, 10% CO2, and 10% H2. The same amount of the homogenate was also cultured aerobically on Columbia Blood Agar (Oxoid) for 7 days at 37° C. in order to detect aerobic bacteria. Following incubation, the bacterial colonies were counted and the quantity of each colonial morphotype was expressed as colony forming units (CFU) per gram of tissue. In the case of *P. acnes* positivity, a single *P. acnes* colony was taken and inoculated on a new anaerobic plate and incubated under anaerobic condition at 35-37° C. until colonies appeared. From inoculated plate, full sterile loop was taken and placed in glycerol serum broth media in 2 mL sterile cryo tube and placed in −80° C. freezer.

Study Participants

Human tissue samples of degenerated Nucleus pulposus (NP) were obtained from 8 patients who underwent microdiscectomy at the University Hospital Brno, Czech Republic.

Isolation and Culture of Human Nucleus Pulposus (NP) Cells

Fresh nucleus pulposus (NP) tissue samples were cut into small pieces using a sterile, individually packaged, gamma-irradiated scalpel and, a sterile, gamma-irradiated petri dish and then digested overnight with collagenase A (Roche) at 37° C. After the digestion, the cell suspensions with undigested tissues were filtered through a cell strainer with pores of 40 µm (Millipore) and centrifuged. The cell pellets were resuspended in Dulbecco's Modified Eagle Medium Nutrient Mixture F-12 (DMEM/F12 (1:1) 1×, Gibco) supplemented with 10% fetal bovine serum and antibiotics penicillin (200 U/ml) and streptomycin (100 U/mL). Cells were cultured at 37° C. in a humified atmosphere with 5% CO2 and were maintained in monolayer culture. In the experiment with antibiotic, 0.25 µg/mL clindamycin treatment was used.

After a few passages, cells were seeded in 6-well plates without antibiotics, allowed to attach overnight and assigned to *Propionibacterium acnes* treatment (ratio of 1:100 and 1:1000). Supplementation with LPS (200 ng/µl, Sigma-Aldrich) served as a positive control, and cells cultured without *P. acnes* served as a negative control. Cells were harvested into Qiazol lysis reagent (Qiagen) and RIPA buffer (Sigma) at four time points: after 3 h, 24 h, 48 h and 1 week.

RNA Isolation

RNA was extracted by use of the Direct-zol RNA kit (Zymo Research) as described in the manufacturer's instructions. The concentration and purity of RNA were determined at 260 and 280 nm using a NanoDrop 2000 (Thermo Scientific).

Quantitative Reverse Transcription Real-Time PCR (qRT-PCR)

The total amount of RNA was subjected to reverse transcription (RT) with the use of High Capacity cDNA Reverse Transcription Kit (Applied Biosystems). RT conditions were as follows: 10 min at 25° C., 2 h at 37° C. 5 min at 85° C. Real-time PCR was performed using TaqMan Gene Expression Master Mix (Applied Biosystems) and primer/probe systems: (Thermo Fisher): interleukin-1β (IL-1β, Hs01555410 ml), interleukin-1α (IL-1α, Hs00174092_m1), interleukin 6 (IL-6, Hs00174131_m1), interleukin 8 (CXCL-8, Hs00174103_m1), chemokine (C—C motif) ligand 2 (CCL2, Hs00234140_m1), chemokine (C—C motif) ligand 3 (CCL3, HS00234142_m1), chemokine (C—C motif) ligand 4 (CCL4, Hs99999148_m1), nerve growth factor (NGF, Hs00171458_m1), Brain-derived neurotrophic factor (BDNF, Hs02718934_s1).

All experiments were performed with glyceraldehyde phosphate dehydrogenase (GAPDH) as internal control using the real-time QuantStudio 12K Flex system (Life Technologies). The fold-change of cDNA expression levels was determined from the obtained ΔΔCt values compared to ΔΔCt values of control samples. The thermal cycling amplification program was as follows: one cycle of 94° C. for 10 min and 40 cycles of 95° C. for 15 s, 60° C. for 60 s. Each sample was tested in triplicate and all real-time PCR reactions were run in duplicates.

Lipase Assay

Lipase activity was measured in cell-free culture supernatants collected at 3 h, 24 h and 48 h time points. The procedure was performed using Lipase Activity Assay Kit II (MAK047, Sigma-Aldrich) according to manufacturer protocol.

Enzyme-Linked ImmunoSorbent Assay (ELISA)

Cell lysates (RIPA, Sigma) were added in duplicates to ELISA plates, each with specific antibody against Human IL-beta (RAB0273A), Human IL-6 (RAB0306), Human IL-8/CXCL8 (RABIL8A), Human MCP-1/CCL2 (RAB0054), Human MIP-1 alpha/CCL3 (RAB0073), and Human MIP-1 beta/CCL-4 (RAB0075). Plates were kept at 4° C. overnight and further proceeded according to manufacturer protocol.

Data Normalization and Statistical Analyses

Student t-test was used for statistical evaluation of qRT-PCR experiments (the values are given as the mean±SD). In all tests the value of p≤0.05 (*), the value of p≤0.01 () or the value of p≤0.001 (*) was considered significant.

Example 2. Mechanism of Nociceptor Activation by *P. acnes*

Live bacteria actively release formylated peptides and secrete a host of virulence factors including pore-forming toxins (PFTs) to facilitate tissue dissemination (See Chiu et al, Nature 2013; 501:52-7). Alpha-hemolysin (Hla) is a PFT secreted by nearly all *S. aureus* strains, playing a role in tissue damage, bacterial spread, and inflammation and it was shown to be one of the mechanisms employed by *S. aureus* to elicit sustained bursts of calcium flux, selectively in capsaicin-responsive neurons (See Chiu et al, Nature 2013; 501:52-7).

Type 1 secretion systems (T1SS) are wide-spread among Gram-negative bacteria. An important example is the secretion of the hemolytic toxin HlyA from uropathogenic strains.

Secretion is achieved in a single step directly from the cytosol to the extracellular space. The translocation machinery is composed of three indispensable membrane proteins, two in the inner membrane, and the third in the outer membrane. The inner membrane proteins belong to the ABC transporter and membrane fusion protein families (MFPs), respectively, while the outer membrane component is a porin-like protein. Assembly of the three proteins is triggered by accumulation of the transport substrate (HlyA) in the cytoplasm, to form a continuous channel from the inner membrane, bridging the periplasm and finally to the exterior. Interestingly, the majority of substrates of T1SS contain all the information necessary for targeting the polypeptide to the translocation channel—a specific sequence at the extreme C-terminus (See Thomas et al, Mol. Cell Res. 2014; 1843:1629-41). From *P. acnes*, PPA1396 seems to resemble this operon structure more. It has also been annotated as hemolysin type A.

In bacteria, protein expression initiates with a formyl-methionine group, the formyl group is then removed post-translationally by peptide deformylase. Formyl peptides can be released from the bacteria either actively or passively as a result of cell death. Neutrophils execute a variety of antimicrobial functions, including the generation of reactive oxygen species (ROS), phagocytosis of pathogens and dead and dying tissue, degranulation with the release of a variety of toxic products, expulsion of neutrophil extracellular traps, and paracrine signaling to recruit other cell types. Neutrophils sense inflammatory stimuli principally within the G protein-coupled receptor (GPCR) family. The first GPCR to be described on the human neutrophil was formyl peptide receptor 1 (FPR1) which, when activated, triggers a wide variety of functions, including chemotaxis, degranulation, ROS production, and phagocytosis. The principal ligands for FPR1 are bacterial and mitochondrial formylated peptides, actively secreted by invading pathogens or passively released from dead and dying host cells after tissue injury. Although it was initially thought that FPR1 only bound N-formylated peptides, it is now widely recognized that the formyl group is not a prerequisite for receptor binding. The N-formylated version of any peptide containing a methionine residue at the 5' terminus is at least 100-fold more potent than the identical nonformylated peptide.

Several short formylated peptide sequences have been identified to elicit a response e.g. fMet-Leu-Phe (fMLF) by activating the formyl peptide receptors, and used routinely as models for the study of these systems. Various other peptides have been identified by studying organisms such as *S. aureus* (See Chiu et al, Nature 2013; 501:52-7) and *L. monycogenes* (See Rabiet et al, Eur. J. Immunol. 2005; 35:2486-95).

In this example, we show that a similar mechanism can exist in *P. acnes*, and which may contribute to chronic pain/inflammation.

Identification of *P. acnes* Formyl Peptides

*P. acnes* strains have a number of proteins that have the fMLF and fMLP pattern which has been identified in *E. coli*, but not fMIFL a pattern derived from *S. aureus*. Nevertheless, as in other bacterial species it is expected that *P. acnes* release formylated peptides to its environment, which can trigger an inflammatory response.

Among these proteins that have the peptides of interest there are two membrane proteins and one secreted. Although these proteins are likely to serve a different function in the cell, it is possible that they can be released to the environment and elicit the neutrophil response. Similarly, a number of hypothetical proteins are detected in the genome, which may play a similar role, however they are not predicted to contain any release mechanism.

TABLE 2

Predicted proteins with formyl peptide motif

| Locus Tag | Gene Product Name | Genome Name | Formylated peptide | Gene Symbol | |
|---|---|---|---|---|---|
| PPA1794 | glutamine--fructose-6-phosphate transaminase | *P. acnes* KPA171202 | MLF | glmS | |
| PPA0175 | cytochrome bd-I ubiquinol oxidase subunit 2 apoprotein (EC 1.10.3.10) | *P. acnes* KPA171202 | MLP | PPA0175 | Membrane protein |
| PPA1643 | D-serine/D-alanine/glycine:proton symporter, AAT family (TC 2.A.3.1.7) | *P. acnes* KPA171202 | MLP | PPA1643 | Membrane protein |
| PPA0473 | DNA or RNA helicase of superfamily II | *P. acnes* KPA171202 | MLP | PPA0473 | |
| PPA0720 | DNA polymerase III, epsilon subunit (EC 2.7.7.7) | *P. acnes* KPA171202 | MLP | PPA0720 | |
| PPA2183 | hypothetical protein | *P. acnes* KPA171202 | MLP | PPA2183 | |
| PPA0854 | hypothetical protein | *P. acnes* KPA171202 | MLP | PPA0854 | |
| PPA0745 | hypothetical protein | *P. acnes* KPA171202 | MLP | PPA0745 | |
| PPA2143 | hypothetical protein (polysaccharide deacetylase/xylanase) | *P. acnes* KPA171202 | MLP | PPA2143 | secreted protein |
| PPA1734 | nucleoside-binding protein | *P. acnes* KPA171202 | MLP | PPA1734 | |
| PPA1371 | putative transferase | *P. acnes* KPA171202 | MLP | PPA1371 | |
| PPA0289 | two component transcriptional regulator, LuxR family | *P. acnes* KPA171202 | MLP | PPA0289 | |

Identification of *P. acnes* Hemolysins

There are at least three proteins annotated as hemolysins in *P. acnes*, which are conserved in all sequenced genomes. Of the three, PPA1396 (and its orthologs) seem to better align to the operon structure of known hemolysins. The gene is predicted to encode an alpha hemolysin, which has been shown to activate nociceptors (See Chiu et al, Nature 2013; 501:52-7).

Notably, there is evidence, that the additional genes also exhibit hemolytic activity.

TABLE 3

Predicted hemolysins

| Locus tag | Annotation |
| --- | --- |
| PPA0565 | hemolysin III |
| PPA0938 | hemolysin |
| PPA1396 | alpha hemolysin |

The three genes are present in all species/strains of *Propionibacterium acnes* (aka *Cutibacterium acnes*).

TABLE 4

Hemolysis genes across *P. acnes* strains

| Genome Name | PPA0938 | PPA1396 | PPA0565 |
| --- | --- | --- | --- |
| Cutibacterium acnes AE1 | 1 | 1 | 1 |
| Cutibacterium acnes KCOM 1861 | 1 | 1 | 1 |
| Cutibacterium acnes PA_12_1_L1 | 1 | 1 | 1 |
| Cutibacterium acnes PA_12_1_R1 | 1 | 1 | 1 |
| Cutibacterium acnes PA_15_1_R1 | 1 | 1 | 1 |
| Cutibacterium acnes PA_15_2_L1 | 1 | 1 | 1 |
| Cutibacterium acnes PA_21_1_L1 | 1 | 1 | 1 |
| Cutibacterium acnes PA_30_2_L1 | 1 | 1 | 1 |
| Propionibacterium acnes 266 | 1 | 1 | 1 |
| Propionibacterium acnes 6609 | 1 | 1 | 1 |
| Propionibacterium acnes ATCC 11828 | 1 | 1 | 1 |
| Propionibacterium acnes C1 | 1 | 1 | 1 |
| Propionibacterium acnes hdn-1 | 1 | 1 | 1 |
| Propionibacterium acnes HL096PA1 | 1 | 1 | 1 |
| Propionibacterium acnes KPA171202 | 1 | 1 | 1 |
| Propionibacterium acnes SK137 | 1 | 1 | 1 |
| Propionibacterium acnes TypeIA2 P. acn17 | 1 | 1 | 1 |
| Propionibacterium acnes TypeIA2 P. acn31 | 1 | 1 | 1 |
| Propionibacterium acnes TypeIA2 P. acn33 | 1 | 1 | 1 |

Publications by Nodzo et al (Am. J. Orthop. Belle Mead N.J. 2014; 43:E93-97) show that more than 50% of examined *P. acnes* strains exhibited hemolytic activity, a population enriched in samples with definite infection. Since hemolysin is ubiquitous in *P. acnes* this result is somewhat unexpected—one would expect that all strains are hemolytic. However, it has been shown that non-hemolytic strains may produce hemolysis when treated with antibiotics or other stress (See Wright et al, Infect. Dis. 2016; 9:39-44).

CONCLUSIONS

Based on bioinformatics analysis and correlation with *S. aureus* findings we predict that *P. acnes* hemolysins play a role in causing chronic pain, and this prediction is supported by the presence of such genes in the *P. acnes* genome, as well as the evidence of their expression. This seems to be a ubiquitous phenotype.

The potential of having formylated peptides playing this role is also present. Since formylated peptides are ubiquitous among bacteria, and *P. acnes* contains at least a few proteins with sequence similar to peptides that have been shown to elicit response. However, it is possible that other sequences can also play a similar role as it has been shown in other studies (See Rabiet et al, Eur. J. Immunol. 2005; 35:2486-95), either actively secreted by the bacterium or as byproducts of protein cleavage.

REFERENCES

1. Morlion B. Chronic low back pain: pharmacological, interventional and surgical strategies. Nat Rev Neurol 2013; 9: 462-473.
2. Stirling A, Worthington T, Rafiq M, Lambert P A, Elliott T S. Association between sciatica and *Propionibacterium acnes*. Lancet 2001; 357: 2024-5.
3. Urquhart D M, Zheng Y, Cheng A C, et al. Could low grade bacterial infection contribute to low back pain? A systematic review. BMC Med 2015; 13:13.
4. Ganko R, Rao P J, Phan K, Mobbs R J. Can bacterial infection by low virulent organisms be a plausible cause for symptomatic disc degeneration? A systematic review. Spine 2015; 40(10): E587-592.
5. Capoor M N, Ruzicka F, Machackova T, et al. Prevalence of *Propionibacterium acnes* in Intervertebral Discs of Patients Undergoing Lumbar Microdiscectomy: A Prospective Cross-Sectional Study. PLoS One 2016; 11: e0161676.
6. Shan Z, Zhang X, Li S, Yu T, Liu J, Zhao F. *Propionibacterium acnes* incubation in the discs can result in time-dependent Modic changes: a long-term rabbit study. Spine (Phila Pa. 1976) 2017; doi: 10.1097/BRS.0000000000002192
7. Aubin G G, Portillo M E, Trampuz A, Corvec S. *Propionibacterium acnes*, an emerging pathogen: From acne to implant infections, from phylotype to resistance. Med Mal Infect 2014; 44:241-250.
8. Li Z J, Choi D K, Sohn K C, et al. *Propionibacterium acnes* activates the NLRP3 inflammasome in human sebocytes. J Invest Dermatol 2014; 134: 2747-56.
9. Kistowska M, Gehrke S, Jankovic D, et al. IL-1β drives inflammatory responses to *Propionibacterium acnes* in vitro and in vivo. J Invest Dermatol 2014; 134: 677-85.
10. Risbud M V, Shapiro I M. Role of cytokines in intervertebral disc degeneration: pain and disc content. Nat Rev Rheumatol 2014; 10: 44-56.
11. Chen Z H, Jin S H, Wang M Y, Jin X L, et al. Enhanced NLRP3, caspase-1, and IL-1β levels in degenerate human intervertebral disc and their association with the grades of disc degeneration. Anat Rec (Hoboken). 2015 April; 298 (4): 720-6.
12. LaRock C N, Todd J, LaRock D L, Olson J, O'Donoghue A J, Robertson A A B, Cooper M A, Hoffman H M, Nizet V. IL-1β is an innate immune sensor of microbial proteolysis. Sci Immunol 2016; 1: eaah3539.
13. Le Maitre C L, Hoyland J A, Freemont A J. Interleukin-1 receptor antagonist delivered directly and by gene therapy inhibits matrix degradation in the intact degenerate human intervertebral disc: an in situ zymographic and gene therapy study. Arthritis Res Ther. 2007; 9: R83.
14. Quero L, Klawitter M, Schmaus A, et al. Hyaluronic acid fragments enhance the inflammatory and catabolic response in human intervertebral disc cells through modulation of toll-like receptor 2 signaling pathways. Arthritis Res Ther 2013; 15: R94.
15. Wang J, Tian Y, Phillips K L, Chiverton N, et al. Tumor necrosis factor α- and interleukin-1β-dependent induction of CCL3 expression by nucleus pulposus cells promotes macrophage migration through CCR1. Arthritis Rheum 2013; 65: 832-42.
16. Freemont A J, Peacock T E, Goupille P, Hoyland J A, O'Brien J, Jayson M I. Nerve ingrowth into diseased intervertebral disc in chronic back pain. Lancet 1997; 350: 178-81.

17. Gruber H E, Hoelscher G L, Bethea S, Hanley E N Jr. Interleukin 1-beta upregulates brain-derived neurotrophic factor, neurotrophin 3 and neuropilin 2 gene expression and NGF production in annulus cells. Biotech Histochem 2012; 87: 506-11.
18. Denk F, Bennett D L, McMahon S B. Nerve growth factor and pain mechanisms. Annu Rev Neurosci 2017; 40:307-325.
19. Chiu I M, Heesters B A, Ghasemlou N, et al. Bacteria activate sensory neurons that modulate pain and inflammation. Nature 2013; 501(7465): 52-57. doi: 10.1038/nature12479.
20. Bruggemann, H., Insights in the pathogenic potential of *Propionibacterium acnes* from its complete genome. Semin Cutan Med Surg 2005; 24: 67-72.
21. Jahns A C, Eilers H, Alexeyev O A. Transcriptome analysis of *Propionibacterium acnes* biofilms in vitro. Anaerobe 2016; 42: 111-118.
22. Nodzo S R, Hohman D W, Crane J K, Duquin T R. Hemolysis as a clinical marker for *Propionibacterium acnes* orthopedic infection. Am J Orthop. 2014; 43(5): E93-E97.
23. Albert H B, Sorensen J S, Christensen B S, Manniche C. Antibiotic treatment in patients with chronic low back pain and vertebral bone edema (Modic type 1 changes): a double-blind randomized clinical trial. Eur Spine J 2013; 22: 697-707.
24. Palazzo C, Ferrari M, Lefevre-Colau M-M, Nguyen C, Rannou F, Poiraudeau S. Lack of effectiveness of antibiotics in chronic low back pain with Modic 1 changes. Joint Bone Spine 2017; 84: 507-508.
25. Zeller V, Ghorbani A, Strady C, Leonard P, Mamoudy P, Desplaces D. *Propionibacterium acnes*: An agent of prosthetic joint infection and colonization. J Infect 2007; 55:119-124.
26. Dinarello C A, Simon A, van der Meer J W. Treating inflammation by blocking interleukin-1 in a broad spectrum of diseases. Nat Rev Drug Discov 2012; 11: 633-52.
27. Eibl J K, Strasser B C, Ross G M. Structural, biological, and pharmacological strategies for the inhibition of nerve growth factor. Neurochem Int 2012; 61: 1266-1275.
28. Katz N, Borenstein D G, Birbara C, Bramson C, Nemeth M A, Smith M D, Brown M T. Efficacy and safety of tanezumab in the treatment of chronic low back pain. Pain 2011; 152:2248-2258.
29. Thomas S, Holland I B, Schmitt L. The Type 1 secretion pathway—The hemolysin system and beyond. Biochim. Biophys. Acta BBA—Mol. Cell Res. 2014; 1843:1629-41.
30. Rabiet M-J, Huet E, Boulay F. Human mitochondria-derived N-formylated peptides are novel agonists equally active on FPR and FPRL1, while *Listeria monocytogenes*-derived peptides preferentially activate FPR. Eur. J. Immunol. 2005; 35:2486-95.
31. Wright T E, Boyle K K, Duquin T R, Crane J K. *Propionibacterium acnes* Susceptibility and Correlation with Hemolytic Phenotype. Infect. Dis. 2016; 9:39-44.

EQUIVALENTS

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

Those skilled in the art will recognize, or be able to ascertain, using no more than routine experimentation, numerous equivalents to the specific embodiments described specifically herein. Such equivalents are intended to be encompassed in the scope of the following claims.

INCORPORATION BY REFERENCE

All patents and publications referenced herein are hereby incorporated by reference in their entireties.

The invention claimed is:

1. A method for treating degenerative disc disease or chronic lower back pain, comprising:
   administering to a patient having degenerative disc disease or chronic lower back pain, and suspected of having a low-virulence infection, an antibiotic and an IL-1β inhibitor; wherein the IL-1β inhibitor is selected from the group consisting of anakinra, canakinumab, gevokizumab, and IL-1trap.

2. The method of claim 1, wherein the patient is suspected of having a low-virulence infection based on the detection of a commensal pathogen in intervertebral disc tissue.

3. The method of claim 2, wherein the commensal pathogen is one or more of *Propionibacterium* sp., *Staphylococcus* sp., *Corynebacterium* sp., *Lactobacillus* sp., *Pseudomonas* sp., *Enterococcus* sp., *Streptococcus* sp., *Bacillus* sp., *Citrobacter* sp., *E. coli*, *Moraxella* sp., *Haemophilus* sp., *Neisseria* sp., *Clostridium* sp., *Enterobacter* sp., and *Klebsiella* sp.

4. The method of claim 3, wherein the commensal pathogen is *Propionibacterium acnes*.

5. The method of claim 4, wherein the low-virulence infection is identified by the presence of one or more virulence factors in the patient's disc tissue.

6. The method of claim 1, wherein the antibiotic is selected from benzylpenicillin, amoxicillin, ampicillin, dicloxacillin, methicillin, nafcillin, oxacillin, penicillin G, cephalexin, cefoxitin, cephalolothin, ceftriaxone, ciprofloxacin, chloramphenicol, erythromycin, tetracycline, vancomycin, clindamycin, fusidic acid, doxycycline, moxifloxacin, linezolid, rifampicin, ertapenem, taurolidine, or a combination thereof.

7. The method of claim 1, wherein the antibiotic is administered systemically or locally.

8. The method of claim 7, wherein the antibiotic is administered by a route selected from oral, parenteral, and transdermal.

9. The method of claim 8, wherein the IL-1β antagonist is administered by a route selected from parenteral, oral, and transdermal.

10. The method of claim 9, wherein the parenteral administration is subcutaneous injection, intramuscular injection, intravenous injection, or local injection to intervertebral disc tissue.

11. The method of claim 1, wherein the antibiotic and the IL-1β inhibitor are co-administered.

12. The method of claim 1, wherein the antibiotic and the IL-1β inhibitor are administered prior to surgery.

13. The method of claim 1, wherein the antibiotic and the IL-1β inhibitor are administered following surgery.

* * * * *